Figure 1:
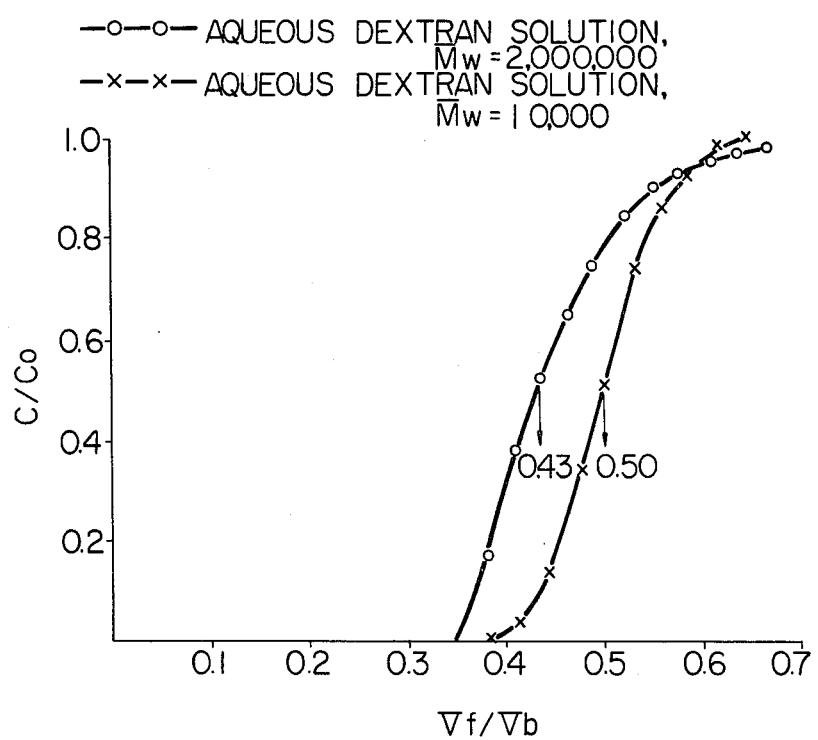

United States Patent [19]

Fujita et al.

[11] 4,078,970
[45] Mar. 14, 1978

[54] INSOLUBILIZED GLUCOSE ISOMERASE

[75] Inventors: Yoshimasa Fujita, Tokyo; Akiyoshi Matsumoto, Hino; Isao Kawakami, Machida; Tadashi Hishida, Tokyo; Akira Kamata; Yusuke Maeda, both of Yokohama, all of Japan

[73] Assignees: Mitsubishi Chemical Industries Ltd.; Seikagaku Kogyo Co., Ltd., both of Tokyo, Japan

[21] Appl. No.: 722,109

[22] Filed: Sep. 10, 1976

Related U.S. Application Data

[63] Continuation-in-part of Ser. No. 561,837, Mar. 25, 1975, abandoned.

[51] Int. Cl.² .............................................. C07G 7/02
[52] U.S. Cl. .................................. 195/63; 195/31 F; 195/68; 195/DIG. 11
[58] Field of Search ............... 195/DIG. 11, 31 F, 63, 195/68

[56] References Cited

U.S. PATENT DOCUMENTS

| | | | |
|---|---|---|---|
| 3,708,397 | 1/1973 | Sipos | 195/31 F |
| 3,788,945 | 1/1974 | Thompson et al. | 195/31 F |
| 3,868,304 | 2/1975 | Messing | 195/31 F |
| 3,960,663 | 6/1976 | Tamura et al. | 195/31 F |

OTHER PUBLICATIONS

Patterson, "Preparation of Cross-Linked Polystyrenes and Their Derivatives for Use as Solid Supports or Insoluble Reagents", Biochemical Aspects of Reactions on Solid Supports, Stark ed., Academic Press, NY and London, (1970) pp. 189-213.

*Primary Examiner*—Alvin E. Tanenholtz
*Assistant Examiner*—Thomas G. Wiseman
*Attorney, Agent, or Firm*—Oblon, Fisher, Spivak, McClelland & Maier

[57] ABSTRACT

There is disclosed a process for producing an insolubilized glucose isomerase useful for converting glucose into fructose comprising contacting a macroporous anion exchange resin with glucose isomerase to effect absorption of the isomerase on the resin, said resin having high porosity and high ion exchange capacity, whereby the resulted insolubilized glucose isomerase has high degree of adsorption, high activity retention and high activity yield.

2 Claims, 1 Drawing Figure

INSOLUBILIZED GLUCOSE ISOMERASE

This invention is a continuation-in-part of U.S. Ser. No. 561,837 filed on Mar. 25, 1975 now abandon.

This invention relates to a process for producing an insolubilized glucose isomerase and, in more particular, to a process for producing an insolubilized glucose isomerase by absorbing glucose isomerase on an ion exchange resin, and to the products prepared by such process.

It has already been known that glucose is converted into fructose by glucose isomerase which is an enzyme capable of converting glucose into fructose and vice versa. Such glucose isomerase has been found in many microorganisms, including the followings: *Streptomyces flavovirens, Streptomyces achromogenes, Streptomyces echinatus, Streptomyces albus, Aerobacter cloacae, Bacillus megaterium, Acetobacter suboxydans, Bacillus fructose* and *Lactobacillus fermenti*, and, for practical purpose, an enzyme obtained from Streptomyces. Glucose isomerase is soluble in water and, therefore, where the conversion of glucose into fructose is enzymatically conducted, it is convenient to subject such enzyme to an appropriate treatment to convert it into an insolubilized or immobilized glucose isomerase which can be used as a solid catalyst. Various processes for such treatment have already been proposed. For example, microbial cells containing glucose isomerase are treated at a specified temperature to effect intracellular fixation of the isomerase such as disclosed in U.S. Pat. No. 3,694,314, glucose isomerase isolated from the cells is adsorbed on a carrier of an anion exchanger, such as DEAE-Sephadex [Journal of Society of Japan Foodstuff Industry 14-12 p. 539 – 540 (1967)] and DEAE-cellulose (U.S. Pat. No. 3,708,397). However, such processes invole inherent disadvantages, for example, as follows: The insolubilized glucose isomerase according to the former process requires a long time for carrying out the conversion of glucose into fructose and further, since the product fructose solution is highly colored, a complicated purification or decoloration treatment is required, thus this process is commercially disadvantageous. On the other hand, DEAE-Sephadex and DEAE-cellulose have tendency to swell in water. Accordingly, the amount of isomerase adsorbed per unit volume of the carrier is relatively small and the larger compressibility of the carrier causes substantial pressure drop during passage of the glucose solution through a column packed with such insolubilized isomerase; thus latter two processes are also disadvantageous.

Another approach is the use of a synthetic anion exchange resin as a carrier on which glucose isomerase is adsorbed. For example, U.S. Pat. No. 3,788,945 and U.S. Pat. No. 3,960,663 deal with an insolubilized isomerase wherein glucose isomerase is adsorbed on a porous anion exchange resin such as Amberlite IRA 938, Amberlite IRA 900 and Amberlite IRA 904. Such anion exchange resin has less tendency to swell in water and therefore it is expected that the isomerization reaction is effectively carried out by a column process where such an anion exchange resin is used as a carrier for the isomerase.

According to U.S. Pat. No. 3,960,663, an insolubilized glucose isomerase is produced by passing an aqueous glucose isomerase solution through a column packed with an anion exchange resin to effect adsorption, and the degree of adsorption of isomerase is as low as 40% and the amount of isomerase adsorbed is also relatively low.

The more the amount of the glucose isomerase adsorbed on a given amount of the carrier resin and the higher the degree of the activity retention, the higher is the isomerization performance of the insolubilized glucose isomerase, and, furthermore, the higher the degree of the adsorption of glucose isomerase, the higher is the efficacy of the glucose isomerase of a given amount.

The inventors have conducted extensive research finding out a process for producing an insolubilized glucose isomerase wherein more glucose isomerase is adsorbed on a given amount of a carrier resin, in higher degree of adsorption and higher degree of activity retention, especially the resulting insolubilized isomerase has an activity yield of more than 40, the activity yield being a value of a hundredth of a product of the degree of adsorption and the degree of activity retention of glucose isomerase and, as the result, it has been found that, among macroporous anion exchange resins, a specific resin having specified values of its porosity and ion exchange capacity has a capability of adsorbing more glucose isomerase per a given amount of the resin. Furthermore, the inventors have found that, when such anion exchange resin is contacted with the glucose isomerase in an amount of from 700 to 5000 U per one milliliter of the resin and more than 50% of the glucose isomerase is adsorbed, the resulting insolubilized glucose isomerase exhibits higher degree of activity retention and more than 50% of the activity yield.

Accordingly, a primary object of this invention is to provide a process for producing an insolubilized glucose isomerase wherein a large amount of isomerase is adsorbed and more than 40% of the activity yield is achieved. Another object is to provide a process for producing an insolubilized glucose isomerase comprising contacting a macroporous anion exchange resn having a porosity of from 4.5 to 20% measured according to the aqueous dextran solution method and an exchange capacity of from 0.035 to 0.1 meq./ml-Resin measured according to the polyanion decomposition method with glucose isomerase of from 700 to 5000 U per one milliliter of the resin at a temperature of from 40° to 75° C and a pH of from 6.5 to 9 until at least 50% of the total isomerase and from 500 to 4000 U of the isomerase per one milliliter of the resin have been adsorbed.

The procedures for carrying out the aqueous dextran solution method and the polyanion salt decomposition method referred to in the specification and claims are defined as follows.

Aqueous dextran solution method

Into a jacketed column of 11 mm internal diameter is packed with 67 ml of an $SO_4$ type anion exchange resin having a void ratio of 33% in wet state to form a resin bed and any excess water is removed while the bed is maintaned at a temperature of 50° C, a 1.5 wt% aqeuous solution of dextran having a weight average molecular weight (Mw) of 2,000,000 determined by the light scattering method is passed through the resin bed at a space velocity (SV) of 0.4 $hr^{-1}$ and the effluent is divided into 2 g fractions. The concentration of each effluent fraction is measured by a refractometer. The quotient obtained by dividing the volume of the effluent (Vf) by the volume of the resin bed (Vb) and the quotient obtained by dividing the dextran concentration of each effluent fraction (C) by the original dextran concentration of 1.5 wt% (Co) are ploted on the horizontal axis and the vertical axis, respectively, to obtain a curve.

Similar procedures are repeated using a 1.5 wt% aqueous solution of dextran having a weight average molecular weight of 10,000 determined by the light scattering method to obtain a curve.

Then, the porosity is determined by dividing by the factor of 0.67 the difference between the values of Vf/Vb at the points where C/Co is 0.5 for each of the aqueous dextran solutions, the molecular weight being 10,000 and 2,000,000, respectively; usually the porosity is expressed by a percentage, so the value determined as above is multiplied by the factor of 100.

The porosity of the resin in the specification and claims is measured by using a Kiriyama column available from Kiriyama Seisakusho, Japan, Dextran T2000 having a weight average molecular weight of 2,000,000 measured by the light scattering method and Dextran T10 having a weight average molecular weight of 10,500 measured by the light scattering method available from Pharmacia Fine Chemicals AB, Uppsala, Sweden and an immersion liquid refractometer type T available from Karl Zweiss A.G. West Germany.

In measuring the porosity of resin, it should be appreciated that a variation in the molecular weight of dextran by ±10% from the abovementioned ranges does not essentially affect the result; the narrower the distribution of the molecular weight, the better the result, but little or no substantial affect is observed by such variation in distribution.

Polyanion salt decomposition method

A given amount of polystyrene having a number average molecular weight ($\overline{M}w$) of 10,000 measured by the vapor pressure method and a value of less than 1.06 obtained by dividing a weight average molecular weight measured by the light scattering method by a number average molecular weight, is subjected to sulfonation with 98% sulfuric acid in an amount of 10 times the weight of said polystyrene and silver sulfate as catalyst in an amount of 0.01 time at a temperature of 100° C for 5 hours. The reaction product is brought to neutral by addition of aqueous ammonia, and water is removed in vacuo to obtain a solid product which is then extracted with methanol. From the extract the methanol is removed in vacuo to obtain ammonium poly(styrenesulfonate). One gram of the ammonium poly(styrenesulfonate) is dissolved in demineralized water to obtain one liter of an aqueous solution. The solution is passed through a jacketed column of 8 mm internal diameter and packed with 10 ml of an OH type anion exhange resin maintained at a temperature of 25° C at a rate of 100 ml/hr for 5 hours. The effluent from the column in an amount of 500 ml is titrated with 1/10N hydrochloric acid using methyl orange as an indicator. The quotient obtained by dividing the amount of the hydrochloric acid required for titration (ml) by the factor of 100 is the ion exchange capacity (meq/ml-Resin).

The resin employed in measuring the ion exchange capacity is Mono-Disperse Polystyrene Standard ($\overline{M}w$ = 10,000 and $\overline{M}w/Mn$ < 1.06) available from Pressure Chemical Co., Ltd. Variation in the average molecular weight by ±10% from the abovementioned range does not essentially affect the results.

Although the mechanism by which glucose isomerase is adsorbed on a macroporous ion exchange resin and the way the enzyme activity is retained have not yet been clarified in detail, it is believed that there is a synergistic effect of physical adsorption in the macropores of the resin and a certain chemical bonding force between anion exchange groups and the enzyme employed. This seems to be true, since very little glucose isomerase is adsorbed on a conventional gel type ion exchange resin which does not have any macropore and, on the other hand, a resin which has macropores but no ion exchange group can adsorb only a small amount of enzyme and the activity of enzyme is also low. Thus, it is believed that the amount of glucose isomerase adsorbed on an anion exchange resin and the degree of the activity retention of the isomerase adsorbed are dependent upon the volume of macropores which plays a role in the adsorption of the isomerase and the number of ion exchange groups in the macropores.

The porosity measured by the aqueous dextran solution corresponds to the total volume of macropores having a specific size through which dextran of $\overline{M}w$ being 10,000 can pass but dextran of $\overline{M}w$ being 2,000,000 cannot pass and such porosity has a close relationship to the amount of glucose isomerase which can be adsorbed on the anion exchange resin, therefore, it is believed that the adsorption of glucose isomerase will occur or will occur mainly in such macropores of specific size. It is further believed that the ion exchange capacity measured according to the polyanion salt decomposition method corresponds to the ion exchange capacity of the total surface area of such specific macropores.

A conventional anion exchange resin prepared by copolymerizing a vinyl monomer and a cross-linkable monomer, such as styrene and divinyl benzene, followed by introducing anion exchange group has some micropores and therefore, it is believed that a polymeric material can contact with only the outer surface but not with the internal surface of the micropores. In this connection, the porosity and the ion exchange capacity above specified of such conventional anion exchange resin which is a gel type is far less than that of the resin of this invention. In contrast, the anion exchange resin employed according to this invention is a macroporous resin and has a large internal surface area.

Such macroporous anion exchange resin is conveniently prepared by any known process, for example, a monovinyl monomer and a cross-linkable monomer are copolymerized in the presence of any material which is removable by a solvent and does not take part in the reaction, such as polystyrene. After completion of the polymerization, the resin obtained is treated with a solvent to extract the material, e.g. polystyrene, and then anion exchange group be introduced. The anion exchange resin thus produced has, in general, macropores the radius of which ranges from about $10^1$ to $10^4$ Angstroms (A). However, it should be noted that among the pores, smaller pores cannot adsorb glucose isomerase whereas much larger pores the internal surface of which is similar to the surface of the gel type anion exchange resin also do not take part in adsorption. This is true, since a certain anion exchange resin which has higher porosity measured according to the mercury penetration method does not necessarily indicate higher adsorption ability for the isomerase. In general, although the pore size and the total pore volume of the macropores in an anion exchange resin may vary depending upon the conditions under which the resin is prepared, such as the amount of a cross-linkable monomer and the amount and the molecular weight of a polymer which is added initially in the polymerization mixture, it is difficult to determine the definite relationship of the pore size and the total pore volume to the preparation conditions.

In this connection, it is desirable to select optimum conditions under which the most appropriate resin is produced by experimental procedures in which various resins are produced by varying preparation conditions and the porosity and the anion exchange capacity are measured according to the abovementioned methods.

In order to introduce anion exchange groups into a matrix resin, it is preferable that the matrix resin be subjected to treatment to introduce chloromethyl group followed by treating with various amine compounds, for example, an aliphatic amine such as trimethylamine, dimethylethanolamine, ethylenediamine, diethylenetriamine and triethylenetetramine, and acyclic amine, such as pyrrolidine, morphorine and piperidine. However, it is appreciated that, if a weak basic amine is employed, there is observed a tendency to a little release of the adsorbed isomerase from the resin, so it is desirable to use a tertiary amine, such as trimethylamine and dimethylethanol amine, to convert the resin into a quarternary ammonium type.

The glucose isomerase which may be employed according to this invention is any of conventional ones produced in the cells of an actinomycete belonging to Streptomyces, such as *St. phaeochromogenus, St. fradiae, St. roseochromogenes, St. olivaceus, St. californicus, St. vinaceus* and *St. albus*. The extraction of glucose isomerase from the microbial cells can be carried out by any suitable known process, such as ultra-sonic treatment, pressurized treatment, mechanical treatment, autolysis and by enzymatic treatment with lysozyme, in particular, the extraction by lysozyme is recommended, since it results in higher extraction of glucose isomerase from the cell, shorter extraction time and a small amount of impurities in the extracted solution.

The glucose isomerase is adsorbed on the macroporous ion exchange resin by any conventional process. The simplest way is to immerse an anion exchange resin in an aqueous solution of glucose isomerase extracted from the microbial cells for a period sufficient to effect adsorption of the isomerase (optionally under agitation) and then wash with water, however, it is preferable to pass and recycle the aqueous glucose isomerase solution upwardly through a column packed with the anion exchange resin to fluidize the resin particles to effect the absorption.

Too small an amount of glucose isomerase is contacted with the anion exchange resin, then only small amount of the isomerase is adsorbed on the resin with the result of a low capability of isomerization by the insolubilized glucose isomerase per a unit volume.

On the other hand, if too large an excessive amount of the isomerase is adsorbed, there is observed lowering the degree of activity retention of the glucose isomerase.

Therefore, according to this invention the amount of glucose isomerase to be contacted with the resin is from 700 to 5000 U, preferably 1000 to 3500 U per 1 ml of the resin and more than 50%, preferably more than 80% of glucose isomerase used is to be adsorbed on the resin.

The adsorption treatment is carried out by using an aqueous glucose isomerase solution at a concentration of from 50 to 1000 U/ml, preferably 150 to 500 U/ml, a pH of from 5.5 to 9.5 and at a temperature of from 40 to 75° C.

In order to assure, more than 50% of glucose isomerase supplied is adsorbed, it is required to contact the aqueous glucose isomerase with the anion exchange resin for a long time. Where in the case of either immersing the resin in the aqueous isomerase solution or passing upwardly the aqueous through a column packed with the resin, the contact time may vary depending upon type of the resin employed, and in general, from 2 to 18 hours is satisfactory under the conditions abovementioned. The aqueous isomerase may be passed through downwardly a column packed with the resin, while the effluent from the bottom is recirculated to the top of the column for about 2 to 18 hours, although the insolubilized isomerase thus obtained lacks uniformity and is less effective.

The anion exchange resin may be a free type, it is preferred to use a salt type, such as $SO_4^-$, $Cl^-$, $PO_4^-$ or $CH_3COO^-$ type which is prepared by treating an anion exchange resin with sulfuric acid, hydrochloric acid, phosphoric acid or acetic acid, since such salt type resin can adsorb more glucose isomerase than a free type.

The anion exchange resin specified according to this invention is capable of adsorbing a large amount of glucose isomerase but, if too large an amount of glucose isomerase is adsorbed on the resin, the degree of the activity retention will lower. Thus, the amount of the glucose isomerase to be adsorbed on the resin is from 500 to 4000 U, preferably 1000 to 3000 U per 1 ml of the resin in wet state.

Because of high degree of the activity retention of the insolubilized isomerase according to this invention, more than 40%, and, by an appropriate selection of the treatment condition, more than 60% of the activity yield can be obtained.

The insolubilized glucose isomerase thus produced possesses a number of advantages which make it possible to carry out the isomerization of glucose into fructose effectively on a commercial basis, for example, higher activity for isomerization of glucose, little or no activity loss for a long time of period, no appreciable release of the isomerase from the carrier resin and little or no coloration of the resulting product. The isomerization is conveniently carried out by a fixed bed system but, because the insolubilized isomerase according to this invention has high mechanical strength and is easy to separate from a slurry, it can be employed in a fluidized bed system, a transfer bed system and a batch system with agitation.

When, the activity of the insolubilized glucose isomerase according to this invention lowers after being used for a long time, it is easy to renew it by releasing the isomerase from the resin by the treatment of an aqueous salt solution such as aqueous sodium chloride, followed by adsorbing fresh isomerase on the resin without loss of its activity.

The insolubilized glucose isomerase produced according to this invention contains a large quantity of isomerase adsorbed on the resin and possesses high activity, therefore, the use of such isomerase in converting glucose into fructose results in many advantages including (1) less anion exchange resin is required for a given amount of fructose, (2) higher space time yield is achieved, (3) due to shorter dwell time of glucose solution in the column, less coloration and lowering of the pH of the product are realized and (4) the pressure drop in the column is decreased. Thus the insolubilized glucose isomerase according to this invention is suitable for use in the conversion of glucose into fructose.

This invention will be explained in detail referring to following Examples without intention to limit this invention.

In the Examples, the activity of glucose isomerase extracted and the activity of insolubilized glucose isomerase, the degree of activity retention and the degree of adsorption of isomerase are defined as follows.

1. Activity of glucose isomerase extracted

A mixture of 0.2 ml of 1 M aqueous D-glucose solution, 0.2 ml of 0.05 M aqueous $MgSO_4 \cdot 7H_2O$ solution, 0.2 ml of 0.5 M aqueous phosphate buffer (pH = 7.2) and a given amount of aqueous solution of extracted glucose isomerase is diluted with water to make it to 2 ml. The mixture is maintained at a temperature of 70° C for 60 minutes to effect the conversion which is terminated by the addition of 2 ml of 0.5 M perchloric acid. The amount of fructose produced is determined by the cystein carbazole method. The value obtained by dividing the amount of fructose produced by the amount of the extracted glucose isomerase solution is the activity, the unit of which is expressed by the abbreviation "U".

2. Activity of insolubilized glucose isomerase

To one liter of an aqueous solution containing glucose, $MgSO_4 \cdot 7H_2O$ and phosphate buffer at a concentration of 0.1 M, 0.005 M and 0.05 M, respectively, is added a given amount of an insolubilized glucose isomerase. The mixture thus obtained is slowly stirred at a temperature of 70° C for 60 minutes to effect the isomerization. Then, the insolubilized isomerase is separated from the reacted solution and the amount of fructose so produced is determined according to the cystein carbazol method. The activity is calculated as in 1 above.

The unit "U" means the amount of glucose isomerase capable of producing one milligram of fructose under the defined conditions.

3. The degree of adsorption of glucose isomerase

The total activity of glucose isomerase solution to be used for adsorption on an anion exchange resin is measured and this value is designated as "A". After adsorption of glucose isomerase on an anion exchange resin, the resin is separated by filtration and washed with water, then the total activity of the combined filtrate and wash water is measured and this value is designated as "B".

The degree of adsorption of glucose isomerase (D.A.G.) is given by the following equation:

$$D.A.G. = A - B/A \times 100 \ (\%)$$

4. Degree of activity retention of insolubilized isomerase

The activity of insolubilized glucose isomerase measured according to 3 above is divided by the activity of extracted glucose isomerase solution to be adsorbed on the resin; the quotient multiplied by 100 is the degree of activity retention expressed as a percentage.

EXAMPLES 1 to 17

One hundred grams of glucose isomerase "NAGASE", which is available from Nagase Sangyo Kabushiki Kaisha, Osaka, Japan, and is produced from *St. phaeochromogenus*, was suspended in 700 ml of demineralized water and, after addition of 80 mg of crystals of egg white lysozyme, the suspension was agitated at 40° C for 45 hours and centrifuged to obtain an extracted solution of glucose isomerase. It was found that the activity of the extracted solution was 200 U/ml. Then, each 50 ml of the extracted solution (the total activity being 10,000 U) was mixed with each of anion exchange resins listed in Table 1 the bed volume of which was 10 ml in wet state and the mixture was agitated at 50° C for 6 hours to effect adsorption of isomerase on the resin to obtain an insolubilized glucose isomerase.

The characteristics of the insolubilized isomerase are also given in Table 1.

Table 1 deals also with Comparative Examples referred to by letters.

In Example 11 and Comparative Examples A to F, the anion exchange resined employed were commercially available.

The anion exchange resins employed in Examples other than Example 4 were produced by a suspension polymerization technique using styrene, divinyl benzene, polystyrene and toluene in water and benzoyl peroxide as catalyst, followed by subjecting particles of styrene-divinyl benzene copolymer to chloromethylation and introducing each of the anion exchange groups listed in Table 1.

The resin of Example 4 was produced by polymerizing a mixture of styrene, divinyl benzene and n-heptane using benzoyl peroxide as catalyst to obtain particles of styrene-divinyl benzene copolymer followed by chloromethylating and introducng anion exchange group.

Resin types of $SO_4^-$, $PO_4^-$, $OH^-$, $Cl^-$ and $CH_3COO^-$ listed in Table 1 mean that the anion exchange resins were treated with 2N-sulfuric acid, 1N-phorphuric acid, 2N sodium hydroxide, 2N-hydrochloric acid and 1N acetic acid, respectively.

According to the aqueous dextran solution method, the porosity of the anion exchange resin exployed in Example 1 was measured. The curves showing relationships between C/Co and Vf/Vb of dextrans of molecular weights of 10,000 and 2,000,000 are shown in the attached drawing.

Table 1

| Example and Comparative Example No. | Characteristics of ion exchange resin | | | | | | Insolubilized glucose isomerase | | | |
|---|---|---|---|---|---|---|---|---|---|---|
| | Degree of Cross-linkage[1] (%) | Anion exchange group | Total ion exchange capacity (meg/ml) | Porosity (%) | Ion exchange capacity (meg/ml) | Type of the matrix | Degree of adsorption (%) | Degree of activity retention (%) | Activity yield | Note |
| 1 | 10 | Trimethyl ammonium type | 0.79 | 10.4 | 0.074 | $SO_4^{--}$ type | 99.9 | 91.0 | 90.9 | |
| 2 | 10 | " | 0.95 | 10.0 | 0.088 | " | 99.7 | 29.1 | 91.8 | |
| 3 | 10 | " | 0.79 | 19.4 | 0.039 | " | 93.7 | 88.2 | 86.6 | |

Table 1-continued

| Example and Comparative Example No. | Characteristics of ion exchange resin | | | | | Insolubilized glucose isomerase | | | |
|---|---|---|---|---|---|---|---|---|---|
| | Degree of Cross-linkage[1] (%) | Anion exchange group | Total ion exchange capacity (meq/ml) | Porosity (%) | Ion exchange capacity (meq/ml) | Type of the matrix | Degree of adsorption (%) | Degree of activity retention (%) | Activity yield | Note |
| 4 | 15 | " | 0.57 | 19.4 | 0.061 | " | 99.8 | 91.5 | 91.3 | |
| 5 | 25 | " | 0.67 | 7.5 | 0.070 | " | 96.3 | 91.1 | 87.7 | |
| 6 | 25 | Dimethyl ammonium type | 0.60 | 13.0 | 0.096 | " | 99.9 | 88.5 | 88.4 | |
| 7 | 10 | Trimethyl ammonium type | 0.79 | 10.4 | 0.074 | $PO_4^{---}$ type | 99.5 | 88.0 | 87.6 | |
| 8 | 10 | | 0.79 | 10.4 | 0.074 | $OH^-$ type | 95.0 | 80.2 | 76.2 | |
| 9 | 10 | | 0.79 | 10.4 | 0.074 | $Cl^-$ type | 100.0 | 90.3 | 90.3 | |
| 10 | 10 | | 0.79 | 10.4 | 0.074 | $CH_3COO^-$ type | 82.4 | 84.7 | 69.8 | |
| 11 | — | Dimethyl ammonium type | — | 16.4 | 0.042 | $SO_4^{--}$ type | 72.3 | 61.7 | 44.6 | Amberleit IRA-93 |
| A | — | Dimethyl ethanol ammonium type | 1.01 | 8.7 | 0.028 | $SO_4^{--}$ type | 0 | — | 0 | Amberleit IRA-910 |
| B | — | " | 0.91 | 15.7 | 0.027 | " | 0 | — | 0 | Amberleit IRA-911 |
| C | — | | 0.53 | 0.7 | 0.034 | " | 10 | 45 | 4.5 | Amberleit IRA-938 |
| D | 8 | Trimethyl ammonium type | >1.3 | 0 | 0.028 | " | 0 | — | 0 | Diaion SA-#100 |
| E | 10 | " | >1.3 | 3.0 | 0.030 | " | 7 | — | — | Diaion PA-320 |
| F | — | " | 1.03 | 16.4 | 0.038 | " | 46.7 | 78.9 | 36.8 | Amberleit IRA-900 |

Note [1] Percentage of the weight of the divinyl monomer to the total weight of the divinyl monomer and monovinyl monomer.

EXAMPLE 12

A glucose isomerase producing strain of *Streptomyces albus* YT-No. 5 which had been deposited with the Fermentation Research Institute, Japan as FERM-P-No. 463 was inoculated on 80 ml of a culture medium which was an aqueous solution containing 1 wt% of polypepton, 0.3 wt% of $K_2HPO_4$, 0.1 wt% of $MgSO_4 \cdot 7H_2O$ and 1 wt% of xylose and cultivation was effected at a pH of 7 and at a temperature of 30° C for 3 hours. Then, 25 ml of the cultivated medium was transferred to 500 ml of a culture medium which was an aqueous solution containing 3% of wheat bran, 2% of corn steep liquor, 0.1% of $MgSO_4 \cdot 7H_2O$ and 0.024%, by weight, of $CoCl_2 \cdot 6H_2O$ and cultivation was continued at a temperature of 30° C for 30 hours. Subsequently, the cultivated culture was centrifuged to collect cells from which, after washing with water, glucose isomerase was extracted according to the procedures as in Example 1, the activation being 230 U/ml-Resin.

The extracted isomerase was adsorbed on the resin as in Example 1 following the procedures of Example 1. It was found that, in the insolubilized isomerase, the degree of adsorption of isomerase was 99.2% and the degree of activity retention and the activity yield were 88.8% and 88.1, respectively.

EXAMPLE 13

The cells of *Streptomyces olivaceus* were subjected to a ultrasonic treatment under the waves of 10 kilocycles per second for 10 minutes, using ultrasonic generator Type N-50-3 available from Toyo Riko Seisakusho, Tokyo Japan, to obtain extracted glucose isomerase solution. One hundred milliliters of such extract, the total activity being 5000 U, was mixed with 4 ml of the resin employed in Example 4 and the mixture was agitated at a temperature of 50° C for 15 hours. It was found that the insolubilized glucose isomerase thus obtained had a degree of adsorption of isomerase, an activity retention and an activity yield of 90%, 87% and 78.3, respectively.

EXAMPLES 14 TO 17 AND G.

According to procedures similar to those of Example 1, glucose isomerase was extracted from glucose isomerase NAGASE, the activity of the extraction being 254 U/ml.

The aqueous glucose isomerase and the anion exchange resin employed in Example 1 were mixed in various proportions for 6 hours to effect the adsorption of isomerase, the proportion and the treating temperature were given in Table 2.

The characteristics of the glucose isomerases thus obtained are given in Table 1.

Table 2

| Example No. | Amount of glucose isomerase used for adsorption (U/ml-Resin) | Temp. (° C) | Degree of adsorption (%) | Degree of activity retention (%) | Activity yield |
|---|---|---|---|---|---|
| 14 | 1016 | 50 | 99.8 | 102.1 | 101.9 |
| 15 | 2032 | 50 | 95.2 | 83.5 | 79.5 |
| 16 | 3429 | 50 | 85.2 | 73.6 | 62.7 |
| 17 | 4826 | 70 | 70.3 | 68.9 | 48.4 |

Table 2-continued

| Example No. | Amount of glucose isomerase used for adsorption (U/ml-Resin) | Temp. (° C) | Degree of adsorption (%) | Degree of activity retention (%) | Activity yield |
| --- | --- | --- | --- | --- | --- |
| G | 6858 | 70 | 50.1 | 60.2 | 30.2 |

What is claimed is:

1. An insolubilized glucose isomerase having an enzymatic activity yield of more than 40 produced by contacting a macroporous anion exchange resin having a porosity of from 4.5 to 20% measured according to the aqueous dextran solution method and an ion exchange capacity of 0.035 to 0.1 meq/ml-Resin measured according to the polyanion salt decomposition method with glucose isomerase in a proportion of from 700 to 5000U per 1 ml of said resin in wet state at a temperature of from 40° C to 75° C, at a pH of from 5.5 to 9.5 for 2 to 18 hours to effect adsorption of more than 50% and from 500 to 4000U of the glucose isomerase per 1 ml of said resin in wet state.

2. An insolubilized glucose isomerase having an enzymatic activity yield of more than 60 produced by contacting a macroporous anion exchange resin having a porosity of from 4.5 to 20% measured according to the aqueous dextran solution method and an ion exchange capacity of from 0.035 to 0.1 meq/ml-Resin measured according to the polyanion salt decomposition method with glucose isomerase in the proportion of from 1000 to 3500U per 1 ml of said resin in wet state at a temperature of from 40° C to 75° C, at a pH of from 5.5 to 9.5 for 2 to 18 hours to effect adsorption of more than 80% of said glucose isomerase supplied and from 1000 to 3000U per 1 ml of said resin in wet state.

* * * * *

UNITED STATES PATENT AND TRADEMARK OFFICE
CERTIFICATE OF CORRECTION

PATENT NO. : 4,078,970

DATED : March 14, 1978

INVENTOR(S) : Yoshimasa Fujita et al

It is certified that error appears in the above-identified patent and that said Letters Patent are hereby corrected as shown below:

In the ABSTRACT, line 5, delete "absorption" and insert --adsorption--.

Column 1, line 8, delete "absorbing" and insert --adsorbing--;

Column 1, line 15, delete "followings" and insert --following--;

Column 1, line 36, delete "invole" and insert --involve--;

Column 2, line 37, delete "resn" and insert --resin--;

Column 3, line 23, delete "Zweiss" and insert --Zeiss--;

Column 4, line 7, delete "macropore" and insert --macropores--;

Column 5, line 19, delete "morphorine" and insert --morpholine--;

Column 5, line 51, delete "absorption" and insert --adsorption--;

Column 6, line 8, after "aqueous" insert --isomerase--;

Column 6, line 19, delete "$C^-$" and insert --$Cl^-$--;

Column 8, line 31, delete "resined" and insert --resins--;

UNITED STATES PATENT AND TRADEMARK OFFICE
CERTIFICATE OF CORRECTION

PATENT NO. : 4,078,970
DATED : March 14, 1978
INVENTOR(S) : Yoshimasa Fujita et al It is certified that error appears in the above-identified patent and that said Letters Patent are hereby corrected as shown below:

Column 8, line 45, delete "introducng" and insert --introducing--;

Column 8, line 48, delete "phorphuric" and insert --phosphoric--;

Table 1, line 7, delete "(meg/ml)" (both instances) and insert --(meq/ml)-- (both instances).

Table 1, line 12, delete "29.1" and insert --92.1--;

Table 1, (continued), under the heading "Note", delete "Amberleit" (in all five instances) and insert --Amberlite-- (in all five instances).

Column 10, line 59, delete "1" and insert --2--.

Signed and Sealed this

*Nineteenth* Day of *December 1978*

[SEAL]

Attest:

RUTH C. MASON
*Attesting Officer*

DONALD W. BANNER
*Commissioner of Patents and Trademarks*